(12) United States Patent
Ellering et al.

(10) Patent No.: US 11,877,769 B2
(45) Date of Patent: Jan. 23, 2024

(54) ATHERECTOMY SYSTEM CURRENT SENSING, PROCESSING AND DISPLAY

(71) Applicant: Cardiovascular Systems, Inc., St. Paul, MN (US)

(72) Inventors: Nicholas Ellering, Crystal, MN (US); Jacob P. Draxler, St. Paul, MN (US); Matthew W. Tilstra, Rogers, MN (US); Joseph P. Higgins, Minnetonka, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 147 days.

(21) Appl. No.: 17/652,381

(22) Filed: Feb. 24, 2022

(65) Prior Publication Data

US 2022/0265310 A1     Aug. 25, 2022

Related U.S. Application Data

(60) Provisional application No. 63/153,689, filed on Feb. 25, 2021.

(51) Int. Cl.
| A61B 17/3207 | (2006.01) |
| A61B 17/00 | (2006.01) |
| A61B 17/32 | (2006.01) |

(52) U.S. Cl.
CPC ........... *A61B 17/320758* (2013.01); *A61B 2017/00119* (2013.01); *A61B 2017/320004* (2013.01)

(58) Field of Classification Search
CPC .. A61B 17/320758; A61B 2017/00123; A61B 2017/320004; A61B 2017/00199; A61B 2017/00022; A61B 2017/00119

USPC .............................................................. 318/3
See application file for complete search history.

(56) References Cited

U.S. PATENT DOCUMENTS

| 10,052,122 B2 * | 8/2018 | Higgins ......... A61B 17/320758 |
| 2010/0286791 A1 | 11/2010 | Goldsmith |
| 2013/0018399 A1 * | 1/2013 | Rivers ............ A61B 17/320758 |
| | | 606/159 |
| 2015/0073447 A1 | 3/2015 | Rydberg et al. |
| 2019/0090901 A1 * | 3/2019 | Piippo Svendsen ........................ |
| | | A61B 17/320758 |

FOREIGN PATENT DOCUMENTS

WO     2019/118522 A1     6/2019

OTHER PUBLICATIONS

International Search Report and Written Opinion issued in PCT/US2022/70832, dated May 18, 2022.

\* cited by examiner

*Primary Examiner* — Kawing Chan
*Assistant Examiner* — Gabriel Agared
(74) *Attorney, Agent, or Firm* — Kagan Binder, PLLC

(57) ABSTRACT

The present invention comprises at least sensing, monitoring, and display of motor current which is then used in various embodiments of a rotational atherectomy device to determine and/or predict, among other things, treatment progression, treatment completion, optimal rotational speed, optimal advancement or traversal speed during treatment, whether stall appears imminent, and/or reacting to stop motor rotation before a stall occurs. In some embodiments, the determination or prediction results in an automatic, or preprogrammed adjustment by the control unit of the rotational speed of the rotating drive shaft and associated tool.

27 Claims, 6 Drawing Sheets

ATHERECTOMY SYSTEM CURRENT SENSING, PROCESSING AND DISPLAY

CROSS-REFERENCE TO RELATED APPLICATIONS

This application claims the benefit of U.S. Provisional Application No. 63/153,689, filed Feb. 25, 2021 and entitled Atherectomy System Current Sensing, Processing and Display, the entirety of which is hereby incorporated by reference.

STATEMENT REGARDING FEDERALLY SPONSORED RESEARCH OR DEVELOPMENT

Not Applicable

BACKGROUND OF THE INVENTION

Generally, atherectomy devices and systems, including but not limited to rotational and/or orbital atherectomy devices ("OAD") use electric motors to power the rotational drive shaft and related abrasive or cutting or sanding element (tool) generally located at a distal location of the drive shaft.

In these procedures, it is highly advantageous to the medical professional operating the device to have data that indicates, inter alia: visual indication of treatment progress using overlapping motor current vs time graphs for each treatment pass through a lesion; when the treatment is complete—or nearing completion; when, or if, the traverse speed should be slowed, or may be increased, and a warning when the device is close to stalling within the patient's blood vessel.

The inventions disclosed herein address these, inter alia, issues.

FIELD OF THE INVENTION

Generally, intravascular atherectomy devices, including but not limited to rotational and orbital atherectomy devices.

DETAILED DESCRIPTION OF THE INVENTION

Figure 1:
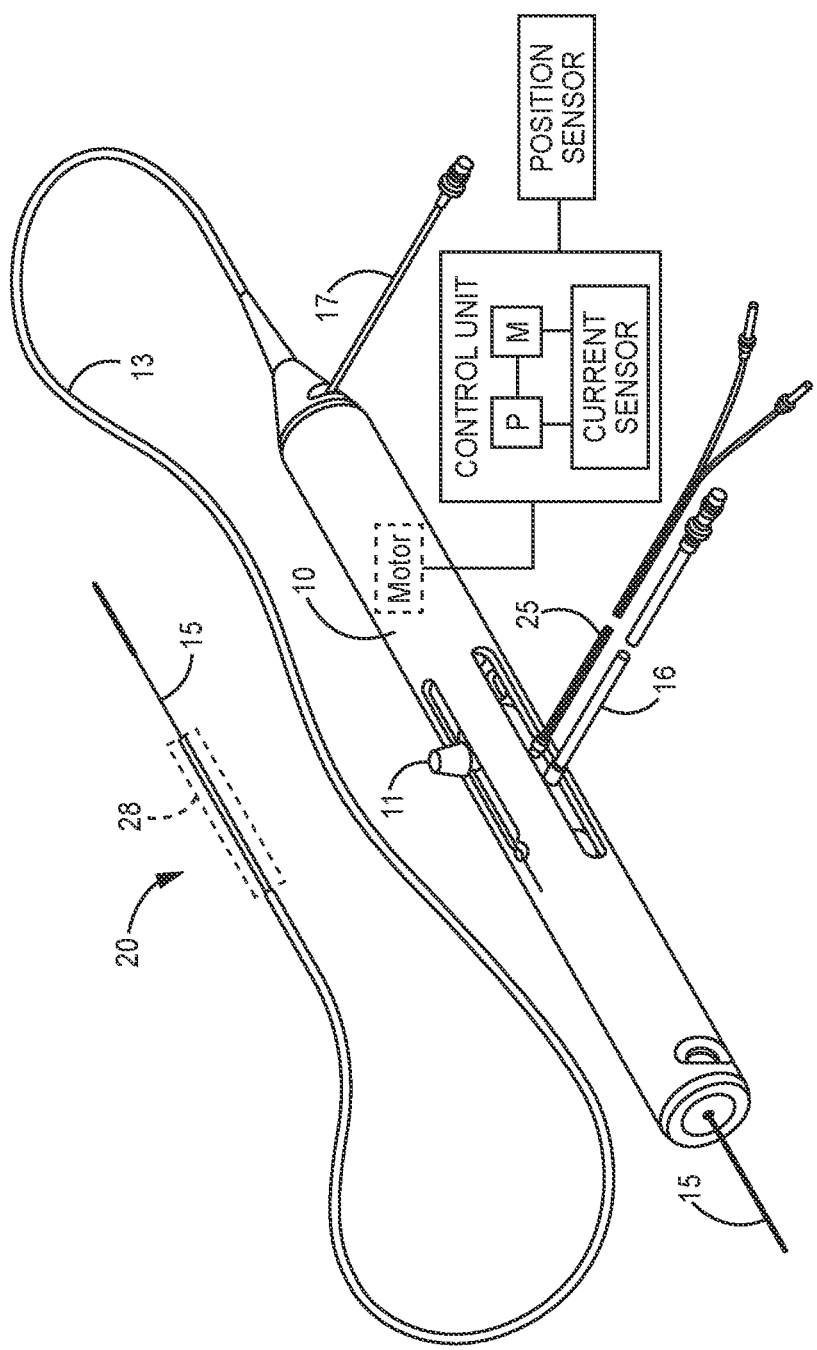
FIG. 1 illustrates one embodiment of the present invention.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives failing within the spirit and scope of the invention.

Various embodiments of the present invention comprise at least sensing, monitoring, and display of motor current which is then used in various embodiments of a rotational atherectomy device to determine and/or predict, among other things, treatment progression, treatment completion, optimal rotational speed, optimal advancement or traversal speed during treatment, whether stall appears imminent, and/or reacting to stop motor rotation before a stall occurs. In some embodiments, the determination or prediction results in an automatic, or preprogrammed adjustment by the control unit of the rotational speed of the rotating drive shaft and associated tool.

FIG. 1 illustrates an exemplary prior art rotational atherectomy device which may, or may not, be an orbital atherectomy device. The device includes a handle portion 10, an elongated, flexible drive shaft 20 having an abrasive section 28, and an elongated catheter 13 extending distally from the handle portion 10. Abrasive section 28 may comprise a single abrasive element such as an abrasive crown or enlarged part of the drive shaft, covered at least in part with abrasive coating such as diamond dust as is known in the art. Alternatively, abrasive section 28 may comprise more than one abrasive element, wherein each abrasive element may be spaced axially from an adjacent abrasive element. Abrasive section 28 may be disposed at, or near, the distal end of drive shaft 20.

Generally, a rotational atherectomy device may comprise an abrasive section that has a center of mass located on an axis of rotation of drive shaft 20 and, in some embodiments, may be disposed at the end of the drive shaft 20. In the case of orbital atherectomy devices, the abrasive section 28 may comprise a center of mass that is radially offset from the axis of rotation of the drive shaft 20, thus creating an imbalance during high-speed rotation of the drive shaft 20. In turn, a working diameter traced by the orbital atherectomy abrasive section 28 may be larger than its resting diameter.

The drive shaft 20 is constructed from helically coiled wire as is known in the art and an abrasive element 28 is fixedly attached thereto. Known drive shafts are manufactured from a multi-filar wound coil which may comprise oppositely-wound filars to minimize elongation or shortening during operation, though filars need not be oppositely wound in drive shaft 20 as is well understood in the art.

Catheter 13 has a lumen in which most of the length of the drive shaft 20 is disposed, except for the enlarged abrading head 28 and a short section distal to the abrasive element 28. The drive shaft 20 also contains an inner lumen, permitting the drive shaft 20 to be advanced and rotated over the guide wire 15. A fluid supply line 17 may be provided for introducing a cooling and lubricating solution (typically saline or another biocompatible fluid) into the catheter 13.

The handle 10 desirably contains a prime mover (motor) such as an electric motor, or turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20. The handle 10 also desirably includes a control knob 11 for advancing and retracting the drive shaft 20 with respect to the catheter 13 and the body of the handle and the abrasive section 28 proximate the distal end of drive shaft 20.

FIG. 1 further comprises a control unit operatively connected with the motor and with a display. Control unit comprises a processor which may contain programmed instructions, wherein the processor is configured to execute the programmed instructions under defined circumstances. Control unit further comprises a memory configured to store sensed data obtained during treatment passes and/or reference table data for comparison with sensed data obtained during treatment passes. Memory is in operative connection with processor.

Control unit further comprises a current sensor for monitoring current at the motor, wherein the current sensor is in operative connection with the processor and with the memory.

Moreover, certain embodiments comprise a position sensor that may be operatively connected or in operative communication with control knob 11 of handle 10, wherein position sensor is further operatively connected or in operative communication with processor and/or memory of control unit. Still further, position sensor may be positioned at any point on or along the drive shaft 20 or on abrasive section and configured to operatively communicate with processor and/or memory of control unit. In certain embodiments, position sensor may be within control unit and in operative communication with control knob 11, drive shaft 20 and/or abrasive section 28. Generally, it is desirable to track the position of the abrasive section 28 during a Pass through a lesion which requires accounting for the length of the drive shaft 20 and/or other intervening structures in some embodiments, e.g., where the position sensor is connected with the control knob 11, to derive the relative starting, intermediary and ending traverse positions for the abrasive section 28 during Passes. An exemplary traverse rate may be 1 mm/second though other rates will be readily apparent to the skilled artisan and which may depend upon a number of factors, including but not limited to the composition of the lesion, rotational speed of the abrasive section and/or structure of the abrasive section.

Figure 5:
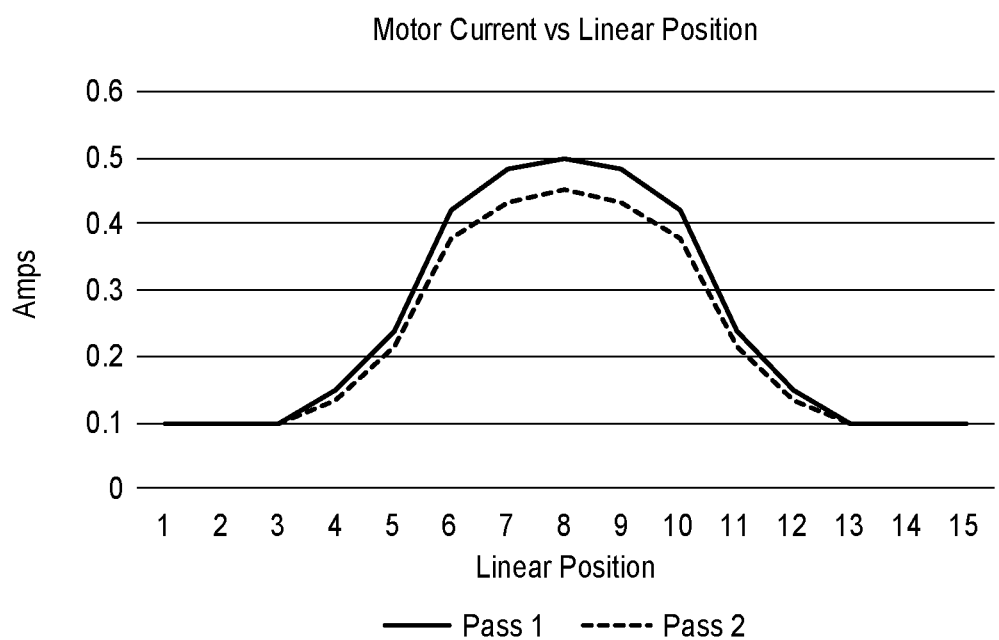
FIG. 5 illustrates an exemplary motor current vs linear position graph over two successive passes through a subject lesion.
Figure 6:
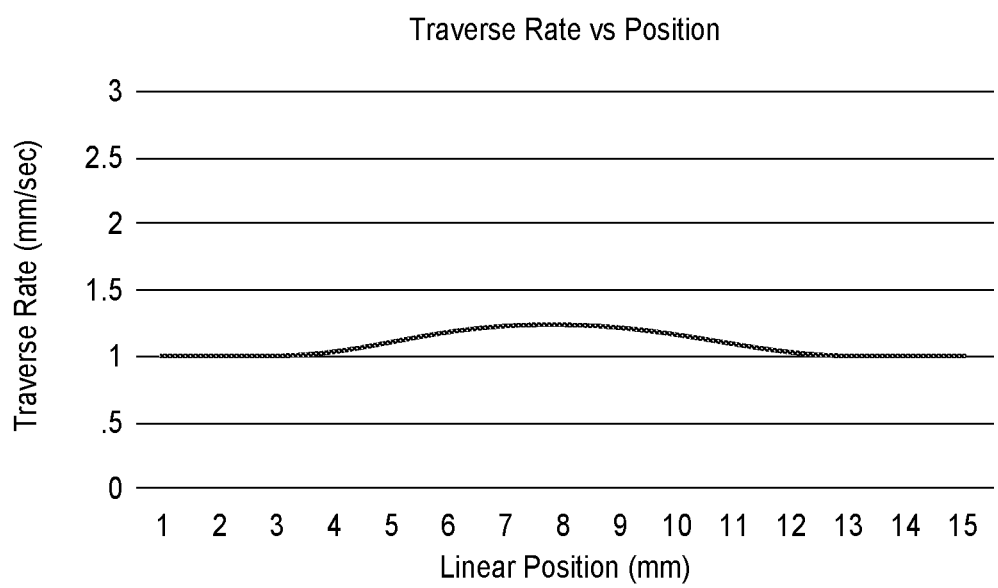
FIG. 6 illustrates an exemplary graph of traverse rate through a subject lesion vs linear position.

Position sensor thus tracks the linear or axial position prior to beginning a Pass and during Passes so that relative position vs time of the abrasive section 28 during a treatment as illustrated in FIG. 5. This allows, in turn, generation of a traverse rate through the subject lumen which may be graphed vs time and displayed on the display as well as communicated to the processor for further analysis as is illustrated in FIG. 6.

Rotational speed of the motor, drive shaft 20 and abrasive section 28 may also be monitored and displayed on the display. Rotational speed may be graphed against motor current, time, and/or linear position of the abrasive section 28; any of these graphs may be displayed on the display.

Figure 2:
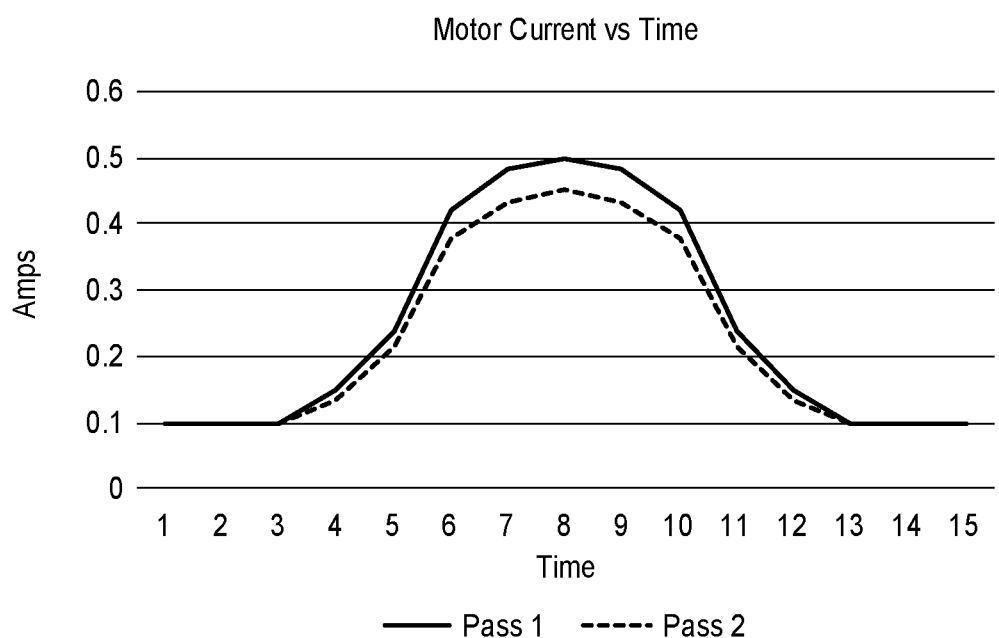
FIG. 2 illustrates an exemplary motor current vs time graph over two successive passes through a subject lesion.

Turning now to FIG. 2, an exemplary theoretical graphing is provided of motor current over time during two treatment Passes through a lesion. As shown, Pass 1 (indicative of one forward pass of the abrasive section 28 through a lesion) generates a higher motor current than does Pass 2 (indicative of a subsequent forward pass of the abrasive section 28 through the lesion). In general, the reduction of motor current in Pass 2 compared with Pass 1 over the same time period indicates that the lesion is being eroded and/or abraded. As the lesion is eroded or abraded, the abrasive section 28 encounters reduced resistance and the motor works at a lower current to produce the same rotational speeds of abrasive section 28.

Thus, both Passes 1 and 2 indicate at time points 1-3 and 13-15 what are essentially flat, stable and non-increasing or non-decreasing motor current levels. Time points 1-3 are motor current levels wherein the abrasive section is rotating within the subject blood vessel, but on the proximal side of the subject lesion, i.e., the lesion has not yet been encountered by the abrasive section 28. Similarly, time points 13-15 also indicate motor current levels that are flat and stable, wherein the abrasive section 28 is not resisted by the subject lesion. The time points between 3 and 13 comprise motor current values that, when graphed over time, comprise a slope, either positive or negative, depending on the trending resistance experienced by the abrasive element 28. Thus, motor current at time points between 3 and 13 are illustrative of the abrasive element 28 moving in a forward pass through a lesion, wherein a peak motor current value is realized roughly at a midpoint between time points 3 and 13. Accordingly, time points 13-15 are providing current motor values wherein the abrasive section 28 is distal of, and clear from, the subject lesion.

The skilled artisan will recognize that as additional Passes beyond illustrated Passes 1 and 2, the motor current will continue to reduce as the lesion is further eroded. In actual practice, at time points 13-15, it is possible that at least some Passes may at least in theory result in a higher, perhaps slightly higher, motor current than time points 1-3, i.e., the motor current is higher when the abrasive section 28 is distal to the lesion as compared when abrasive section is proximal to the lesion. This is because for some Passes, the drive shaft 20 itself may encounter rotational resistance due to the lesion. Accordingly, an optimal motor current indicating a completion of the lesion abrading or erosion by rotating abrasive section 28 therein is illustrated at the baseline levels of exemplary time points 1-3, in the illustrated graph, an exemplary motor current of approximately 0.1 amps.

Figure 3:
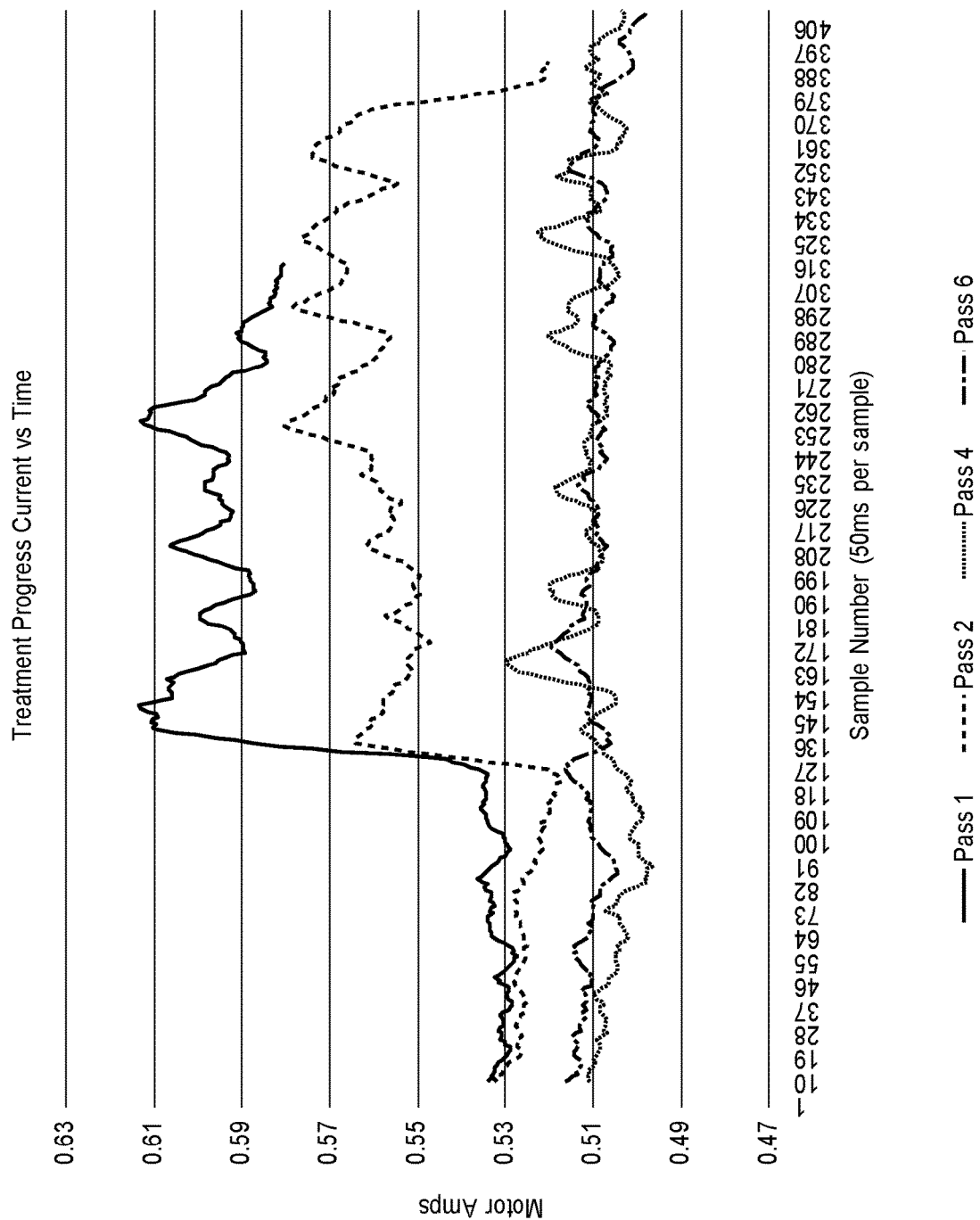
FIG. 3 illustrates an exemplary set of passes through a subject lesion with overlaid graphs of motor current vs time.

Turning now to FIG. 3, actual measured motor current vs time through a lesion is graphed over four illustrated Passes 1, 2, 4 and 6; Passes 3 and 5 are omitted to provide clarity and promote explanation of the illustrated data. Certain embodiments of the current invention may display current vs time data similar to that of FIG. 3, wherein all, or some, of the Passes are graphically displayed for the operator to observe in real time during a treatment of an occluded vascular lesion.

Thus, similar to FIG. 2, the Pass data of FIG. 3 indicates a reduction of motor current with each illustrate Pass, i.e., Pass 1 motor current greater than Pass 2 Motor current. Accordingly, abrasive section 28 encounters greater resistance in the lesion during Pass 1 as compared with Pass 2. Similar to FIG. 2, the motor current for Passes 1 and 2 at a point proximal of the lesion, here approximately sample numbers 1 to approximately 118 are relatively flat and generally the same, i.e., 0.53 or 0.52 amps. And, Passes 4 and 6 also show the same current level flatness through the sample numbers corresponding to 1 to 118, wherein motor current amps are approximately 0.51 to 0.50.

Between sample numbers 118 and approximately 361, motor current is elevated above the motor current measured at points prior to sample 118, indicating that the abrasive section 28 is encountering resistance within the subject lesion, wherein Pass 1 motor current is greater than Pass 2 motor current.

Passes 4 and 6 are illustrative in that the difference between maximum and minimum current values between sample numbers 127 and approximately 370 in Pass 4 appear to be larger than those of Pass 6, indicating that abrasive section 28 does encounter some discrete regions of resistance in the lesion during Pass 4 which appear to be dissipated or smoothed as shown in Pass 6 motor current. For example, Pass 4 quickly, i.e., at a high rate of change, moves from slightly under 0.51 amps at sample number 154 to 0.53 amps at sample 164. Other examples of this non-smoothed minimum to maximum at a high change rate are provided throughout the remainder of Pass 4. In contrast, Pass 6 appears much smoother, with smaller min to max differences. Thus, the motor current as measured and illustrated is relatively sensitive to discrete regions or lengths within a lesion that may require additional treatment.

Generally, motor current and rotational motor speed and/or drive shaft rotational speed (RPM) may be graphed over time for individual Passes through a lesion. This data may be used as an early warning of a potential drive shaft and/or abrasive section 28 stall, wherein the abrasive section 28 become effectively stuck within the lesion while the motor continues to apply torque to the proximal end of the drive shaft and may either wind up or compress the drive shaft much like a spring, with large amounts of stored, potential, energy. If allowed to continue, the stalled abrasive section 28 may suddenly release which, in turn, releases the stored, potential energy of the attached drive shaft 20 and may cause trauma to the patient. In some cases, depending on the winding construction of the drive shaft 20, i.e., oppositely wound or non-oppositely wound filars for example, the drive shaft 20 may "jump" forward or backward after such an energy release post-stall, causing the abrasive section 28 to jump forward or backward within the lesion. In addition, the drive shaft 20 may "ring" after release from a stall, wherein the drive shaft 20 winds and unwinds as it seeks equilibrium. In some cases, the ringing drive shaft 20 may shorten and lengthen, causing related axial movement of the abrasive section 28. All of these unmanaged stall releases are uncontrolled and may cause patient trauma.

Figure 4:
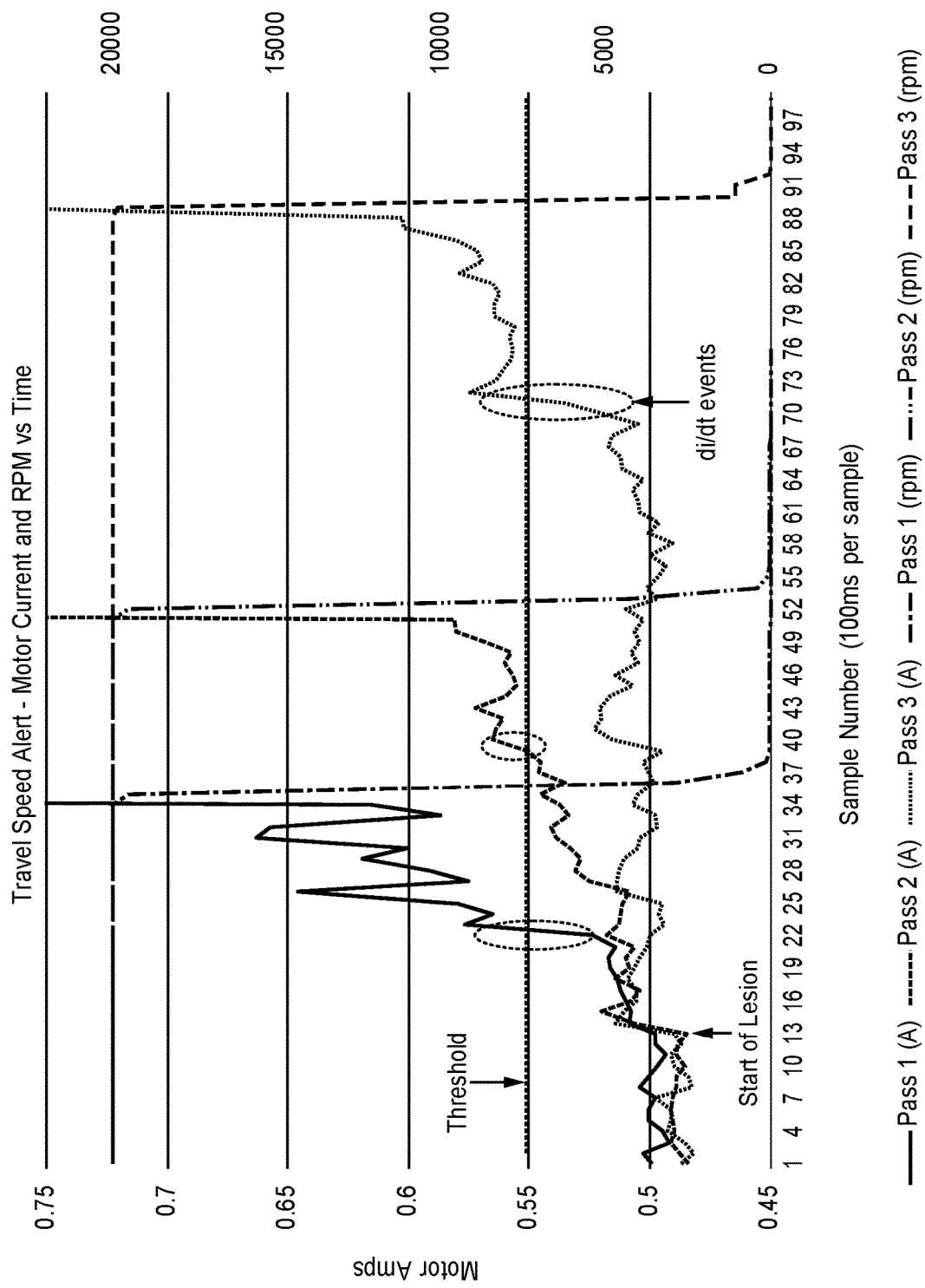
FIG. 4 illustrates an exemplary set of passes through a subject lesion with overlaid graphs of motor current and RPM vs time.

Thus, the early warning of a stall of FIG. 4 is highly desirable.

As in FIGS. 2 and 3, the motor current of Pass 1 is higher generally than motor current of Pass 2 which comprises generally a higher motor current than Pass 3. Here, the start of the lesion is marked at approximately sample number 13. Each of Passes 1, 2 and 3 ultimately stall. Pass 1 stalls at approximately sample number 37, Pass 2 at approximately sample number 52 and Pass 3 at approximately sample number 88. After each Pass stalls, the RPM drops virtually immediately to zero and remains at zero through the remaining sample numbers. All of these graphed data may be displayed on the display to allow the operator to visualize the current movement in real time.

Certain embodiments, e.g., FIG. 3, align the start time for each Pass so that the overlapping displayed Passes may be more readily and accurately compared when displayed and further analyzed by the processor's programmed instructions.

Alternative embodiments may also display a graph of sensed current vs sensed linear or axial position of the abrasive section, whereby an operator may monitor progress and/or the control unit, specifically the processor, may be configured to automatically interrupt power/voltage to the motor if the predetermined maximum current threshold and/or predetermined rate of change of current as a function of linear position is/are exceeded.

There are two early stall warning components shown in FIG. 4, which may be employed together, to warn of a likely imminent stall, allowing the control unit, and/or the operator, to stop application of voltage and/or current to stop rotation of the drive shaft 20 and attached abrasive section 28 before the stall occurs. In this sense, embodiments of the invention predict stall events, allowing the control unit and/or operator to interrupt or stop voltage application to the motor, thereby stopping rotation of the motor, drive shaft 20 and abrasive section 28.

The first early stall warning component comprises establishing a motor current threshold which is a predetermined current level that is established at a predetermined motor current level above the established motor current baseline, i.e., the relatively flat and unchanging motor current values before the abrasive section 28 encounters the lesion. In FIG. 4, this is the region of sample numbers from 1 to about 13, where the start of lesion is marked. Generally, the baseline motor current is approximately 0.48 amps and, based on the baseline motor current, a threshold is established at, in this case, 0.55 amps. Thus, in this exemplary case, the threshold is established at about 0.07 amps above the baseline motor current. However, the threshold may be established at a motor current that is about 0.05 amps, or 0.10 amps, or 0.15 amps above the baseline motor current. Generally, the threshold motor current may be established anywhere between 0.02 to 0.20 amps above a baseline motor current. In some embodiments, a reference library may be stored in the memory of control unit, or may be stored in a remote server or database that is accessed via wired or wireless communication for use by the processor to derive the threshold motor current level that may be appropriate for a given rotational and/or orbital rotational atherectomy system's components, including but not limited to the running baseline current levels at a point proximal of the lesion (discussed further infra), the outer diameter of the drive shaft 20 and its length, the location of the subject lesion, the access point in the patient's body, the type and structure of the abrasive section 28, to mention a few potentially relevant elements. Thus, the processor may execute a look-up in the reference library to obtain one or more threshold motor current levels for a given procedure.

The baseline motor current may be established by prior experimentation, by reference to a reference library or data set of the particular rotational and/or orbital atherectomy system running in vasculature without lesion resistance, or may be established for the particular patient by rotating the actual rotational and/or orbital atherectomy system at a point in the patient's vasculature that is both proximate and proximal to the lesion. In some embodiments, the baseline motor current provides a baseline of the actual rotational and/or orbital atherectomy system's running current, i.e., current at a treatment-level RPM which further considers the running resistance of the system. In an actual patient, running resistance may account for many device and/or patient-specific factors such as, and without limitation, specific patient vascularity and tortuosity thereof, access site location, i.e., femoral vs radial, etc., drive shaft and abrasive section outer diameter sizes, drive shaft length, abrasive section length, abrasive section comprising one or more than one abrasive element, whether abrasive section is orbital, i.e., center of mass radially spaced off the rotational axis of the drive shaft, or non-orbital, i.e., center of mass on the rotational axis of the drive shaft, location of the abrasive section relative to the distal end of the drive shaft, to mention a few factors. Each of these factors has nothing to do with the behavior of the device or system within the subject lesion, rather each factor relates to the individual patient and/or the specific device or system being used.

Alternatively, the baseline current level may be established, or provisionally established, through use of a reference library may be stored in the memory of control unit, or may be stored in a remote server or database that is accessed via wired or wireless communication for use by the processor to derive one or more likely baseline current levels that may be appropriate for a given rotational and/or orbital rotational atherectomy system's components, including but not limited to the running baseline current levels at a point proximal of the lesion (discussed further infra), the outer diameter of the drive shaft 20 and its length, the location of the subject lesion, the access point in the patient's body, the type and structure of the abrasive section 28, to mention a few potentially relevant elements. Thus, the processor may execute a look-up in the reference library to obtain one or more baseline current levels for a given procedure.

The second early warning stall component comprises the rate of change of current, as illustrated in dashed ovals, one or a series of "di/dt events" wherein the rate of change of current over time exceeds a predetermined rate of change threshold. The predetermined rate of change may be established based on prior-obtained data using a particular atherectomy device or system or may be established with reference to a reference data library.

As will be understood by the artisan, the reference data libraries discussed herein may be established as an effectively closed library of data, or may be initially established, but as the treatments are executed across a range of patients, lesions, locations, device and the like, the reference data libraries may be updated to become more precise and more accurate to aid in making the next treatment data set more effective.

As shown by the dashed ovals, in each Pass of FIG. 4, there is at least one "di/dt event" wherein the rate of change of current over time exceeds the predetermined rate of change threshold.

As illustrated, if both the threshold motor current level is exceeded and the predetermined rate of change threshold are exceeded, then the system may alert the operator and/or automatically shut off voltage to the motor, thus stopping the application of torque by the motor to the drive shaft 20 and abrasive section 28 prior to the occurrence of the predicted stall. The amount of time between the sensed exceeding of the threshold motor current and predetermined rate of change threshold is: for Pass 1 approximately 900 ms; for Pass 2 approximately 900 ms; and for Pass 3 approximately 1,000 ms. This is the amount of time, i.e, post-warning, pre-stall window, then that the system and/or operator has to interrupt voltage to the motor to stop applying torque of the motor to the drive shaft and abrasive section 28. As the artisan will recognize, the post-warning, but pre-stall time window magnitude will vary and depends upon a number of factors, including but not limited to the translational speed of the abrasive section 28 through the lesion, the rotational speed of the abrasive section, the composition of the lesion, the structure and effectiveness of the abrasive section 28 for the particular lesion, and/or the torquability and other characteristics of the drive shaft 20.

Certain embodiments may comprise programmed instructions that receive sensed current and/or time and/or position data as described above and compare the received data against a baseline current as described above. If, for example, the sensed current at a time or set of time points and/or at a linear position or positions (generally within the lesion) is greater than the baseline current, e.g., greater than a predetermined allowed current differential, the processor of the control unit may initiate a displayed instruction to continue with at least one more treatment Pass and/or recommend increasing or decreasing the traverse rate or the rotational speed. Other embodiment may comprise determination of whether the sensed current maximum to minimum within the lesion is greater than a predetermined allowable difference with the baseline current maximum to minimum, then the processor of the control unit may initiate a displayed instruction to continue with at least one more treatment Pass and/or recommend increasing or decreasing the traverse rate or the rotational speed. Still further, certain embodiment may comprise the processor calculating the standard deviation of the sensed current within the lesion and, if the standard deviation is greater than either a predetermined magnitude or greater than a calculated standard deviation of the baseline current, then the processor of the control unit may initiate a displayed instruction to continue with at least one more treatment Pass and/or recommend increasing or decreasing the traverse rate or the rotational speed.

In some embodiments where the determination is made by the programmed instructions of the processor of the control unit that, based on sensed current within the lesion, rotational speed should be reduced to avoid a stall, for example, the processor may initiate instruction to the motor to reduce rotational speed to the recommended level, whereby the motor automatically executes the rotational speed reduction without operator intervention. As discussed in connection with FIG. 4, such an automatic reduction, or stoppage, of motor rotational speed may be critical in preventing unwanted and potentially harmful abrasive section 28 stalls within a lesion.

Certain embodiments may determine that the motor current sensed within a Pass is within predetermined limits. In this case, the processor of the control unit may initiate a displayed instruction that the treatment is complete.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. A medical device system comprising:
   a rotational atherectomy device comprising an elongated flexible drive shaft and an abrasive section disposed at or near a distal end of the drive shaft, the drive shaft rotationally driven at a proximal end by an electric motor by application of torque to the drive shaft;
   a control unit operatively connected with the electric motor, the control unit comprising a memory, a processor comprising preprogrammed executable instructions and in operative connection with the memory, and a current sensor operationally connected with the memory, processor and/or motor and configured to sense the current generated by the electric motor;
   a display connected with the control unit,
   wherein the control unit is configured to generate, in real time, individual plots of the sensed current vs time, wherein each one of a plurality of the generated individual plots of the sensed current vs time are overlaid and displayed on the display in real time for each of a plurality of rotational atherectomy treatment passes comprising the abrasive section traversing a lesion, wherein a maximum motor current threshold and a maximum rate of change of current threshold are established and stored within the memory or processor;

wherein if the sensed current exceeds both the maximum motor current threshold and the maximum rate of change current threshold at the same time, the processor is configured to execute instructions that detect an imminent stall of the abrasive section within the lesion.

2. The medical device of claim 1, wherein the processor is configured to execute instructions to annunciate the detected imminent stall by displaying a warning on the display.

3. The medical device of claim 1, wherein the processor is configured to execute instructions to automatically interrupt voltage to the electric motor such that the electric motor stops all application of rotational torque to the drive shaft.

4. The medical device system of claim 1, wherein the displayed overlaid plurality of individual plots of the sensed current vs time are used by an operator to determine progression of the atherectomy rotational treatment.

5. The medical device system of claim 1, wherein the processor is operationally connected with a linear position sensor that is configured to sense a change in axial position of the abrasive section during the treatment passes through the lesion, wherein the processor is configured to execute instructions to generate real time individual plots of the sensed current vs sensed axial position for each one of the plurality of treatment passes.

6. The medical device of claim 5, wherein the processor is configured to execute instructions to overlay each of the generated individual plots of the sensed current vs sensed axial position, and display the overlaid plots of the sensed current vs sensed axial position in real time on the display.

7. The medical device system of claim 4, wherein the overlaid plurality of individual plots of the sensed current vs axial position are used by an operator to determine progression of the atherectomy rotational treatment.

8. The medical device system of claim 5, wherein the control unit is further configured to calculate a plurality of linear travel rates of the rotational atherectomy device based on the sensed axial positions over a period of time.

9. The medical device system of claim 8, wherein the control unit is further configured to generate and display real time individual plots of the sensed current vs linear travel rate for a plurality of the treatment passes.

10. The medical device system of claim 8, wherein the control unit further comprises a predetermined maximum current threshold, wherein if the sensed current exceeds the maximum current threshold, the control unit is configured to alert the operator to reduce the linear travel rate of the atherectomy device.

11. The medical device system of claim 8, wherein the control unit is configured to monitor the rate of change of current and further comprising a predetermined maximum rate of current change, wherein if the predetermined maximum rate of current change is exceeded, the control unit is configured to alert the operator to reduce the linear travel rate, reduce the rotational speed of the electric motor, and/or interrupt power/voltage to the electric motor.

12. The medical device system of claim 10, wherein the control unit is configured to automatically reduce the rotational speed of the motor and/or interrupt voltage to the electric motor.

13. A medical device system comprising:
a rotational atherectomy device comprising an elongated flexible drive shaft and an abrasive section disposed at or near a distal end of the drive shaft, the drive shaft rotationally driven at a proximal end by an electric motor;

a control unit operationally connected with the electric motor, the control unit comprising a memory, a processor operationally connected with the memory, and a current sensor operationally connected with the memory and/or processor and configured to sense the current generated by the electric motor;

a display connected with the control unit,
wherein the processor is configured to issue instructions to generate, in real time, individual plots of the sensed current vs time, wherein each one of a plurality of the generated individual plots of the sensed current vs time are overlaid and displayed on the display in real time for each of a plurality of rotational atherectomy treatment passes comprising the abrasive section traversing a lesion, and wherein the processor is further configured to execute instructions to determine the progress of the treatment based on the sensed motor current and to display the determined progress of the treatment on the display.

14. The medical device system of claim 13, wherein the processor is further configured to execute instructions to provide recommendations to modify the treatment based on the sensed motor current.

15. The medical device system of claim 14, wherein the provided recommendations comprise at least one of the group consisting of: reducing motor rotational speed; increasing rotational speed, increasing linear traverse speed, decreasing linear traverse speed, and stopping rotation of the motor.

16. The medical device system of claim 13, wherein the determined progress is that the treatment is complete.

17. The medical device system of claim 14, wherein the provided recommendations comprise performance of at least one additional treatment pass.

18. The medical device system of claim 13, wherein the processor is operationally connected with a linear position sensor that is configured to sense a change in axial position of the abrasive section during treatment passes through the lesion, wherein the processor is configured to execute instructions to generate real time individual plots of the sensed current vs sensed axial position for each one of the plurality of rotational atherectomy treatment passes.

19. The medical device system of claim 18, wherein the processor is further configured to execute instructions to provide recommendations to modify the treatment based on the sensed motor current.

20. The medical device system of claim 18, wherein the provided recommendations comprise at least one of the group consisting of: reducing motor rotational speed; increasing rotational speed, increasing linear traverse speed, decreasing linear traverse speed, stopping rotation of the motor.

21. The medical device system of claim 18, wherein the determined progress is that the treatment is complete.

22. The medical device system of claim 13, wherein the provided recommendations comprise performance of at least one additional treatment pass.

23. The medical device system of claim 18, wherein the control unit is further configured to calculate a plurality of linear travel rates of the rotational atherectomy device based on the sensed axial positions of the abrasive sections over a period of time.

24. The medical device system of claim 23, wherein the processor is further configured to execute instructions to provide recommendations to modify the treatment based on the sensed motor current.

25. The medical device system of claim 24, wherein the provided recommendations comprise at least one of the group consisting of: reducing motor rotational speed; increasing rotational speed, increasing linear traverse speed, decreasing linear traverse speed, stopping rotation of the motor.

26. The medical device system of claim 23, wherein the determined progress is that the treatment is complete.

27. The medical device system of claim 24, wherein the provided recommendations comprise performance of at least one additional treatment pass.

* * * * *